(12) United States Patent
Yalin

(10) Patent No.: US 10,241,037 B2
(45) Date of Patent: Mar. 26, 2019

(54) LASER SENSOR FOR TRACE GAS DETECTION

(71) Applicant: COLORADO STATE UNIVERSITY RESEARCH FOUNDATION, Fort Collins, CO (US)

(72) Inventor: Azer P. Yalin, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 15/520,051

(22) PCT Filed: Oct. 20, 2015

(86) PCT No.: PCT/US2015/056495
§ 371 (c)(1),
(2) Date: Apr. 18, 2017

(87) PCT Pub. No.: WO2016/064897
PCT Pub. Date: Apr. 28, 2016

(65) Prior Publication Data
US 2017/0336320 A1   Nov. 23, 2017

Related U.S. Application Data

(60) Provisional application No. 62/066,684, filed on Oct. 21, 2014.

(51) Int. Cl.
 *G01N 21/3504* (2014.01)
 *G01J 3/42* (2006.01)
 (Continued)

(52) U.S. Cl.
 CPC .......... *G01N 21/3504* (2013.01); *G01J 3/42* (2013.01); *G01N 21/39* (2013.01);
 (Continued)

(58) Field of Classification Search
 CPC .......................... G01J 3/42; G01N 2201/1248
 See application file for complete search history.

(56) References Cited

U.S. PATENT DOCUMENTS 6,610,982 B2    8/2003  Hoult
7,259,856 B2    8/2007  Kachanov et al.
7,277,807 B2   10/2007  Dieterle et al.

OTHER PUBLICATIONS

International Search Report and Written Opinion, as issued in connection with International Patent Application No. PCT/US2015/056495 dated Mar. 17, 2016, 12 pgs.

(Continued)

*Primary Examiner* — Tri Ton
*Assistant Examiner* — Rufus Phillips
(74) *Attorney, Agent, or Firm* — Maschoff Brennan; Paul G. Johnson

(57) ABSTRACT

Systems and methods are disclosed to determine the concentration of a species within a sample. An example method may include collecting optical loss data over a range of frequencies from the sample using a spectroscopy system; placing the optical loss data into a plurality of bins, each bin having a defined frequency width; determining an average optical loss data value for the optical loss values within each bin that have an optical loss value less than a threshold value; removing the optical loss data within each bin having a value outside a tolerance range bounding the average optical loss data value for the respective bin; fitting a spectral curve to the remaining optical loss data; and determining the concentration of the species within the sample based on the spectral curve.

6 Claims, 11 Drawing Sheets

(51) Int. Cl.
*G01N 21/39* (2006.01)
*G01J 3/28* (2006.01)
(52) U.S. Cl.
CPC . *G01J 2003/2869* (2013.01); *G01J 2003/423* (2013.01); *G01N 2201/1248* (2013.01)

(56) References Cited

OTHER PUBLICATIONS

CA Examiners Report in Canadian Patent Application No. 2965328 dated Jul. 7, 2017, 4 pages.
Wada, et al., "Measurement of IO radical concentrations in the marine boundary layer using a cavity ring-down spectrometer," Journal of Atmospheric Chemistry, vol. 58, Issue 1, pp. 69-87, 2007 (19 pgs).
Bitter, et al., "A broadband cavity ringdown spectrometer for in-situ measurements of atmospheric trace gases," Atmos. Chem. Phys., 5, 2547-2560, 2005 (14 pgs).
He, et al. "Remote open-path cavity-ringdown spectroscopic sensing of trace gases in air, based on distributed passive sensors linked by km-long optical fibers," Opticals Express, vol. 22, Issue 11, pp. 13170-13189, 2014 (20 pgs).
Pettersson, et al. "Measurement of aerosol optical extinction at 532 nm with pulsed cavity ring down spectroscopy," Journal of Aerosol Science, vol. 35, Issue 8, pp. 995-1011, 2004 (17 pgs).
Singh, et al. "Error Analysis and Uncertainty in the Determination of Aerosol Optical Properties Using Cavity Ring-Down Spectroscopy, Integrating Nephelometry, and the Extinction-Minus-Scattering Method," Aerosol Science and Technology vol. 48, Issue 12, pp. 1345-1359, 2014 (53 pgs).
Cui, et al. "Extinction measurement with open-path cavity ring-down technique of variable cavity length," Optics Express, vol. 24, Issue 12, pp. 13343-13350, 2016 (8 pgs).
Gordon, et al. "Design of a Novel Open-Path Aerosol Extinction Cavity Ringdown Spectrometer," Aerosol Science and Technology, 49:9, 717-726, 2015 (11 pgs).
Moosmuller, et al. "Cavity Ring-Down and Cavity-Enhanced Detection Techniques for the Measurement of Aerosol Extinction," Aerosol Science and Technology vol. 39, Issue 1, pp. 30-39, 2005 (11 pgs).
Shadman, et al. "Open-path cavity ring-down spectroscopy sensor for atmospheric ammonia," Applied Physics B, 122:194 2016 (9 pgs).

LASER SENSOR FOR TRACE GAS DETECTION

CROSS-REFERENCE TO RELATED APPLICATIONS

This application is a U.S. National Stage filing under 35 U.S.C. § 371 of International Application No. PCT/US2015/056495, filed on Oct. 20, 2015, which in turn claims the benefit of, U.S. Provisional Patent Application Ser. No. 62/066,684 filed Oct. 21, 2014, the entirety of which is incorporated herein by reference for all purposes.

STATEMENT AS TO RIGHTS TO INVENTIONS MADE UNDER FEDERALLY SPONSORED RESEARCH AND DEVELOPMENT

This invention was made with government support under Grant No. 2012-67021-19978 awarded by the USDA National Institute of Food and Agriculture. The government has certain rights in the invention.

BACKGROUND

The detection of gases in the atmosphere and elsewhere is an important and challenging task that may be important for academic research, public policy, environmental regulation, and private industry. With the increased attention being given to global climate change and atmospheric chemistry, trace gas systems that detect greenhouse and pollutant gases such as, for example, methane, oxides of nitrogen, carbon monoxide, carbon dioxide, and certain acids such as hydrogen chloride are needed. In addition, there are many industrial applications for trace gas sensors such as, for example, to monitor industrial gas leakage, for process monitoring, and/or process control.

One specific example, methane leakage and emission is receiving substantial attention given the rapid growth in use and extraction of natural gas. In addition to providing energy independence by reducing import needs, natural gas is potentially very attractive from the point of view of climate and environmental sustainability since natural gas (methane) combustion produces only half of the carbon dioxide ($CO_2$) emissions compared to coal on a per unit energy basis. On the other hand, the greenhouse gas emissions benefits of natural gas are substantially diminished, potentially even becoming a net detriment depending on the levels of leakage since one methane molecule provides greater than 20 times the radiative forcing of one carbon dioxide molecule.

SUMMARY

Systems and methods are disclosed that can determine the concentration of a species in a gaseous sample. An example method may include collecting optical loss data over a range of frequencies from the sample using a spectroscopy system; placing the optical loss data into a plurality of bins, each bin having a defined frequency width; determining an average optical loss data value for the optical loss values within each bin that have an optical loss value less than a threshold value; removing the optical loss data within each bin having a value outside a tolerance range bounding the average optical loss data value for the respective bin; fitting a spectral curve (of loss or absorption versus laser frequency) to the remaining optical loss data; and determining the concentration of the species within the sample based on the spectral curve.

In some embodiments, the method may further comprise collecting temporal decay data from a sample using a spectroscopy system; and converting the temporal decay data to optical loss data.

In some embodiments, the spectroscopy system comprises a cavity ring-down spectroscopy system. In some embodiments, the concentration of the species within the sample is determined based on spectral peaks due to absorption lines within the spectral curve. In some embodiments, the spectral curve is fitted to the remaining optical loss using a least squares technique.

Some embodiments may include a method for determining the concentration of a species within a sample. The method, for example, may include collecting optical loss data over a range of frequencies from the sample using a spectroscopy system; fitting a first spectral curve to the optical loss data; removing a plurality of optical loss data values having a value greater than a sum of a corresponding value of the first spectral curve plus a tolerance value (e.g., a positive tolerance value); fitting a second spectral curve to the remaining optical loss data; removing a plurality of optical loss data values having a value greater than a sum of a corresponding value of the second spectral curve plus a tolerance value; and determining a second concentration of the species within the sample based on the second spectral curve.

In some embodiments, the method may further include fitting a third spectral curve to the optical loss data; and removing a plurality of optical loss data values having a value greater than a sum of a corresponding value of the third spectral curve plus a tolerance value.

In some embodiments, the method may further include repeating the following until a stop event occurs: fitting a third spectral curve to the optical loss data; removing a plurality of optical loss data values having a value greater than a sum of a corresponding value of the third spectral curve plus a tolerance value; and determining a third concentration of the species within the sample based on the third spectral curve. In some embodiments, the stop event may occur when a concentration difference between the second concentration and the third concentration is below a defined value. In some embodiments, the stop event comprises determining when the number of iterations reaches a predetermined value. In some embodiments, the stop event may comprise when a quality measure of the second spectral curve is above a threshold value.

Some embodiments may include a method for determining the concentration of a species within a sample. The method, for example, may include collecting optical loss data over a range of frequencies from the sample using a spectroscopy system; determining a probability density of the optical loss data; and determining the concentration of the species within the sample based on the probability density.

In some embodiments, determining a probability density of the optical loss data may further comprise: placing the optical loss data into a plurality of bins, each bin having a defined frequency width and a defined optical loss width; and counting the number of optical loss data points within each bin. In some embodiments, the probability density may comprise a three dimensional map of counts within each bin.

In some embodiments, the method includes fitting a spectral surface, containing information on species concentrations, to the probability density.

These illustrative embodiments are mentioned not to limit or define the disclosure, but to provide examples to aid understanding thereof. Additional embodiments are discussed in the Detailed Description, and further description is provided there. Advantages offered by one or more of the various embodiments may be further understood by examining this specification or by practicing one or more embodiments presented.

BRIEF DESCRIPTION OF THE FIGURES

These and other features, aspects, and advantages of the present disclosure are better understood when the following Detailed Description is read with reference to the accompanying drawings.

DETAILED DESCRIPTION

Systems and methods are disclosed to determine the concentration of a species within a sample. In some embodiments, a light source (e.g., a laser) may be directed toward a sample and the frequency of the laser may be swept across a desired frequency range. The desired frequency range, for example, may include frequencies of absorption feature(s) of the target analyte(s). In some embodiments, the ring-down times of the sample may be sampled and converted to optical loss values for each frequency that the laser sweeps across. The optical loss values may be influenced by the optical extinction of aerosol particles within the ambient air. The optical extinction of aerosols may be due to absorption and/or Mie scattering, and/or may depend on the size distribution, complex index-of-refraction, and/or morphology of the particles.

In some embodiments, the total light extinction of aerosols within the sample can be found from the size distribution as:

$$\alpha_{ext} = \int N(D_p)\sigma_{ext}dD_p,$$

where N is the number of particles per unit volume with mean diameter $D_p$, and extinction cross section $\sigma_{ext}$, dependent on the laser frequency, complex refractive index and morphology of the particle. This equation assumes a single species of aerosol composition. If different compositions are present then the contributions from each may be separately found. Given the unknown and varying nature of the aerosol distributions in a sample such as, for example, ambient air, this equation cannot generally be used for a priori calculation. The magnitude of the optical extinction provided by the aerosols may depend on the laser wavelength and the air sample (e.g., pristine air versus polluted air). For typical conditions, for example, the aerosol extinction coefficients may have a value in the range of $\sim 10^{-8}$-$10^{-7}$ $cm^{-1}$ (for 532 nm light). This level of extinction may be far larger than the sensitivity level of some spectroscopy systems meaning, for example, it can be readily detected. This optical extinction may be filtered out of the sampled optical loss data in order to retrieve concentrations not affected by the optical extinction of these aerosols.

Some embodiments of the invention may measure the concentration of various species within a gaseous sample. These species, for example, may include aerosols, methane, carbon monoxide, carbon dioxide, ethane, other hydrocarbon species such as alkanes, water, greenhouse gases, ozone, oxides of nitrogen (e.g., $NO_2$, $NO_3$, $N_2O_5$, etc.), ammonia, volatile organic compounds (VOCs), acids such as hydrochloric acid or nitric acid, and other atmospheric species etc. In some embodiments, the concentration of these species may be measured using a spectroscopy system such as, for example, a cavity ring-down spectroscopy (CRDS) system and the sampled data may be filtered to remove optical loss data points that have been influenced by noise.

Figure 1:
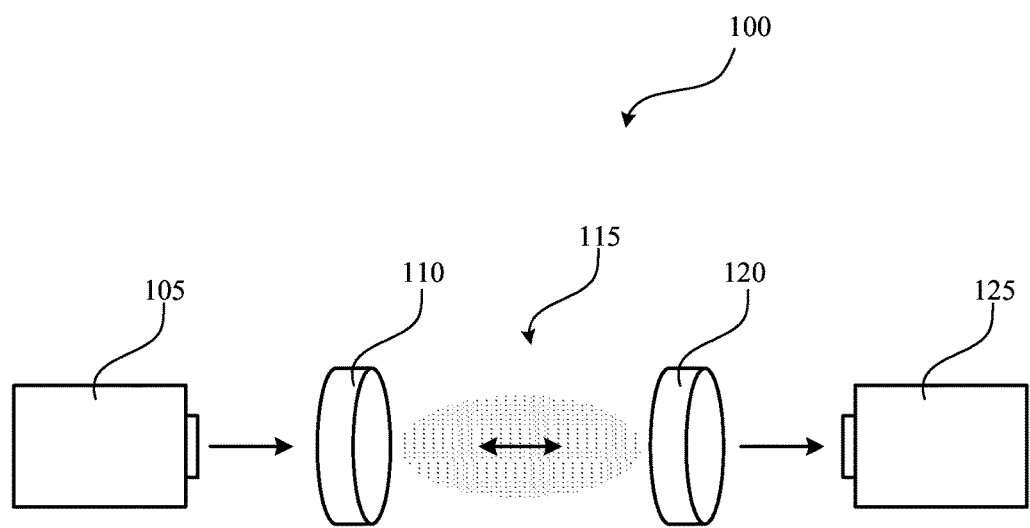
FIG. 1 is a block diagram of an example CRDS system according to some embodiments.

FIG. 1 is a block diagram of an example CRDS system 100 that includes a light source 105, a target volume 115 that is bound at least in part by two reflectors 110 and 120, and a detector 125. The target volume 115 may include any type of sample gas such as, for example, ambient air or atmospheric gases. The CRDS system 100, for example, may be used to measure trace species in a sample in the gas phase. Some possible advantages of the CRDS system 100 may include selectivity, direct quantitative detection of trace species based on known absorption cross sections, and/or the possibility of versatile sensor hardware (small, lightweight, low power consumption) for field use.

In some embodiments, the target volume 115 may, for example, be a high-finesse optical cavity. In some embodiments, the CRDS system 100 may be an open path CRDS system. In some embodiments, the target volume may not include a physical enclosure.

The light source 105 may be any light source such as, for example, a laser light source, that can be tuned across a plurality of wavelengths. The light source 105, for example, may include a diode laser, vertical cavity surface emitting laser (VCSEL), intra-band cascade laser (ICL), a quantum-cascade laser (QCL), difference-frequency generation laser, lead-salt laser, antimonide laser, dye laser, fiber laser which can be in configurations including distributed feedback (DFB) lasers or external cavity diode lasers etc. The light source 105 may emit light of any wavelength such as, for example, an infrared wavelength (2-15 microns), short wavelength infrared (1.4-3.0 microns), mid-infrared (3-8 microns), or long wavelength infrared (8-15 microns).

The light source 105 may emit light into the target volume 115. The light may be reflected back and forth within the target volume 115 a number of times, N, such as, for example, N>10,000 as its light intensity decays in the target volume 115. Because the light is reflected back and forth within the target volume 115 N times, the light may have an effective path length that is approximately N times the path length of the target volume 115. The long effective path length allows for sensitive detection. In CRDS, for example, the detection is via measurement of the decay time of light within the target volume, where the 1/e time is termed the ring-down time.

To accomplish this longer effective path length, for example, the reflectors 110 and 120 may have a reflectivity, for example, of R<0.9999. In some embodiments, the reflectors 110 and 120 may have a reflectivity, for example, of R<0.999 or R<0.99999. In some embodiments, the reflectors 110 and 120 may have a reflectivity, for example, of R>0.9 or R>0.99. In some embodiments, the reflectivity of the reflectors 110 and 120 may have a defined reflectivity within a given and/or specific spectral region(s).

The detector 125 may detect the temporal decay, 1/e (or ring down time, $\tau$) of the light intensity. For example, the light source 105 may be periodically extinguished (for example, for ~10 us to ~10 ms). The light source 105 may be extinguished, for example, with an optical modulator, such that the light inside the target volume can decay to yield the ring-down signal. The intensity of the trapped pulse within the target volume 115 will decrease by a fixed (fractional) amount each round trip within the target volume 115 due to absorption and/or scattering of the sample in the target volume 115 and/or reflectivity losses (e.g., of the two reflectors 110 and 120). The intensity of light, l(t) (or ring down signal), within the target volume 115 may be determined as an exponential function of time, t:

$$I(t) = I_0 e^{(-t/\tau(v))},$$

and $$\frac{1}{\tau(v)} = \frac{c}{l}(k(v)l + (1-R)),$$

where $\tau(v)$ is the 1/e time of decay (or the ring down time), l is the target volume length, c is the speed of light, k(v)l is the absorbance of the sample within the target volume 115, and (1-R) is the single pass target volume loss. k(v) is the absorption coefficient or the extinction coefficient. R may include all losses in the target volume including the reflectivity losses of the reflectors 110 and 120 as well as Rayleigh scattering, diffractive loss, and other wavelength-independent losses. The product of kl+(1-R) is the optical extinction loss (per pass within the target volume), and can be found as $$\frac{l}{c}\tau.$$

Figure 2:
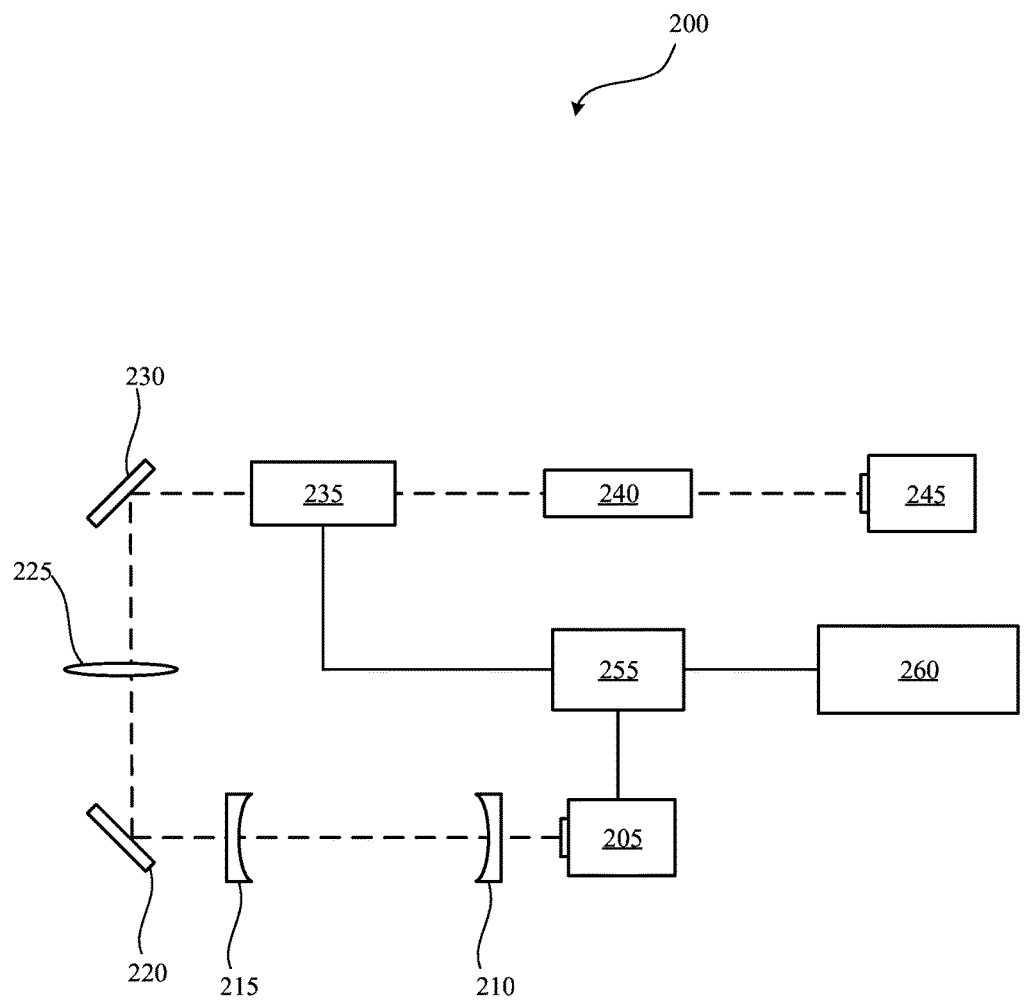
FIG. 2 is a block diagram of another example CRDS system according to some embodiments.

FIG. 2 illustrates another example CRDS system 200. In some embodiments, CRDS system 200 may include a light source 245. The light source 245 may include any type of light source such as, for example, any of the light sources noted above in regard to light source 105. The light source 245, for example, may be a distributed feedback (DFB) interband cascade laser (ICL) producing light at ~3300 or ~3600 nm. The light source 245, for example, may have an output power greater than 0.5, 1.0, 2.0, 5.0, 10.0, 20.0, 50.0 100.0 mW, a linewidth less than or equal to 25, 15, 10, 5, 3, 2, 1, etc. MHz, and/or a mode-hop free tuning range greater than 10, 25, 50, 60, 100, etc. GHz.

The CRDS system 200 may also include an isolator 240. The isolator 240 may be internal or external to the light source 245. The isolator 240 may be used to minimize feedback of back-reflected beams, for example, from the reflector 215, to the light source 245. In some embodiments, such feedback may perturb the power or frequency of the light source 245 leading to noise or fluctuations in the measured ring-down spectra. Desired isolation can be in the range of at least 10-100 dB or 30-60 dB. The isolator 240, for example, can be formed from a combination of polarizers and Faraday rotators, or quarter wave-plate and polarizer. The method of isolation may also be achieved without an actual isolator device but rather with a three-mirror cavity and/or off-axis injection to a two-mirror cavity.

The CRDS system 200, for example, may include one or more acousto-optic modulators 235 (e.g., a Bragg grating) that may be used to diffract and shift the frequency of the light from the light source 245 (e.g., using sound waves). In some embodiments, the one or more acousto-optic modulator 235 may enable narrow line width single-frequency output and continuous (mode-hop free) tuning without the need for an external cavity (moving parts).

In some embodiments, the one or more acousto-optic modulator 235 may be electrically coupled with the triggering circuit 255, which may control the operation of the one or more acousto-optic modulator 235. In some embodiments, light from the light source 245, for example, may be swept across a range of frequencies using the acousto-optic modulator 235.

In some embodiments, the one or more acousto-optic modulator 235 may be used to extinguish the light being delivered to the target volume so that the light decay in the target volume (or the ring-down signal) can be measured. In some embodiments, the acousto-optic modulator 235 may be operated such that the first-order diffraction beam is directed to the target volume (and detector 205). The acousto-optic modulator 235 may be turned off using the triggering circuit 255, which may cut off the beam to the target volume. In some embodiments, the one or more acousto-optic modulator 235 may have a fast switching (extinction) time (e.g., less than about 1 microsecond). In some embodiments, the one or more acousto-optic modulator 235 may have a diffraction efficiency (e.g., greater than 70% of the light into the first-order beam, though lower would also be possible). In some embodiments, the one or more acousto-optic modulator 235 may include an acousto-optic modulator driver.

In some embodiments, the CRDS system 200 may have a mass less than about 10, 5, 3, 1 kg, etc. In some embodiments, the CRDS system 200 may have a power-draw below 5, 10, 20, 30, 40, 50, 60, 70, 80, 90 W, etc.

Various optical elements may be used to direct the light to a target volume bounded by reflectors 215 and 210. These optical elements, for example, may include mirrors 230 and 220 and/or one or more lenses 225, which may, for example, be used to match the size and position of the beam to that which can circulate within the target volume.

The mirrors 230 and 220 may define the target volume and/or may be similar to and/or have the same properties as reflectors 110 and 120. For example, the mirrors 230 and 220 may have a reflectivity, for example, of R<0.9999. In some embodiments, the reflectors 110 and 120 may have a reflectivity, for example, of R<0.999 or R<0.99999. In some embodiments, the reflectors 110 and 120 may have a reflectivity, for example, of R>0.9 or R>0.99. In some embodiments, the reflectivity of the mirrors 230 and 220 may be defined within a given and/or specific spectral region(s).

The mirrors 230 and 220 may define the target volume. The target volume may or may not include any or all of the following: a purge port, a pump, a diaphragm pump, a filter, a vacuum system, a closed flow cell, flow cells, etc. The mirrors 230 and 220 may be separated by 10, 25, 50, 100, 200, 500 cm.

In some embodiments, the target volume defined may, for example, be considered a high-finesse optical cavity. In some embodiments, the CRDS system 200 may be an open path CRDS system.

The detector 205 may include any type of photodetector such as, for example, a photovoltaic detector, a photodiode, a photomultiplier tube, a photosensor, an active pixel detector, a charged coupled device (CCD), a CMOS image sensor, etc. For example, the detector 205 may be a two-stage thermoelectrically cooled photovoltaic detector. In some embodiments, the detector 205 may include one or more amplifiers or filters such as, for example, a low-noise high-bandwidth preamplifier.

In some embodiments, the triggering circuit 255 may monitor the target volume transmission in order to determine when to trigger the acousto-optic modulator 235 to extinguish the light beam emitted from the light source 245. In some embodiments, the light source 245 may be scanned over the targeted region (~0.1-1.0 cm$^{-1}$) at a rate of about 10, 15, 30, 50, 100 times per second. In some embodiments, wavelength calibration may be performed by passing the light beam through an etalon or Fabry-Pérot interferometer of known free spectral range. Calibration may be simultaneous with the measurements or done periodically.

In some embodiments, a microcontroller 260 may be electrically coupled with the triggering circuit 255, the light source 245, and/or the detector 205. The microcontroller 260, for example, may control the operation of the triggering circuit 255, the light source 245, and/or the detector 205. The microcontroller 260 may comprise any or all the components of the computational unit 1100 of FIG. 11.

The detector 205 may collect intensity data and/or the ring-down time as a function of the frequency of the light emitted from the light source 245. In some embodiments, the detector 205 may operate with a high bandwidth (e.g., 50 MHz) and/or a low noise-equivalent-power (e.g., ~0.03 μW).

In some embodiments, the microcontroller 260 may sample a signal from the detector 205 at any sampling rate such as, for example, about 0.1, 1, 10, 25, 50, 100, 200 MHz. The sampled data may be stored in a data logger and/or a memory coupled with the microcontroller 260. The ring-down time can be determined from the raw ring-down (time decay) signals by fitting a function.

In some embodiments, an analog circuit may be coupled with the detector 205 that produces the derivative of the logarithm of the sampled signal. The analog circuit may be sampled at any sampling rate such as, for example, about 0.1, 1, 10, 25, 50, 100, 200 MHz. The sampled data may be stored in a data logger and/or memory coupled with the microcontroller 260. In some embodiments, the ring-down time can be determined from the raw ring-down (time decay) signal by taking the derivative (slope) of the logarithm of the sampled signal While the CRDS system 100 or CRDS system 200 has been described, any other type of spectroscopy system may be used. For example, other cavity enhanced systems may be used such as, for example, integrated cavity output spectroscopy (ICOS) or cavity enhanced absorption spectroscopy (CEAS). In some embodiments, the CRDS system 100 may or may not include vacuum devices or equipment. In some embodiments, the CRDS system 100 may or may not include closed flow cells or similar devices. Other absorption measurement methods may include, for example, wavelength modulation spectroscopy (WMS) with Herriot cells, multi-pass cells, White cells, or Pfund cells that can be used to in increase the optical path length.

In some embodiments, the CRDS system 100 or CRDS system 200 may be coupled with a manned aircraft, a drone, or an unmanned aircraft. In some embodiments, the CRDS system 100 may be a terrestrial system or a desktop system.

Some embodiments may be used for measurement of gas concentrations in the atmosphere (e.g., methane and ethane) as a function of height in the atmosphere with conventional aircraft or UAVs for comparison against column LIDAR measurements.

Some embodiments may be used for identification and/or quantification of emissions and hot-spots of methane above landfills, urban areas, and/or natural gas pipelines and facilities by flying the lightweight sensors on UAVs.

Some embodiments may be used for the simultaneous measurement of both methane and ethane. In some embodiments, the simultaneous ethane and methane measurement may be used to differentiate sources for example methane emission from petrochemical versus agricultural sources.

Some embodiments may be used for measurement of quantitative emission measurements from natural gas facilities based on control-volume approaches and/or the use of atmospheric dispersion models that combine concentration data (above background levels) with wind speed data.

Some embodiments may be used for detection and/or coarse quantification of hot-spots above pipelines and facilities using, for example, airborne lightweight sensors on UAVs. Some embodiments may be used to detect hot spot emissions.

Some embodiments may be used to measure direct eddy flux covariance by combining the sensor concentration measurements with a wind-speed anemometer.

Some embodiments may be used to make quantitative flux measurements from natural gas facilities. The quantitative flux measurements, for example, may be are based on combining concentration data (above background levels). Fluxes can be determined by obtaining data across upwind and downwind transects.

Figure 3A:
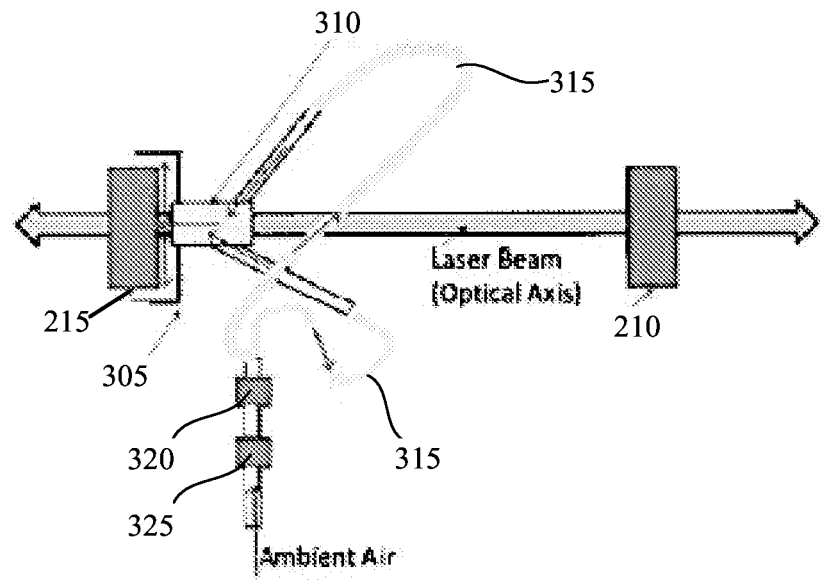
FIG. 3A and FIG. 3B illustrate some techniques for keeping reflectors clean according to some embodiments.
Figure 3B:
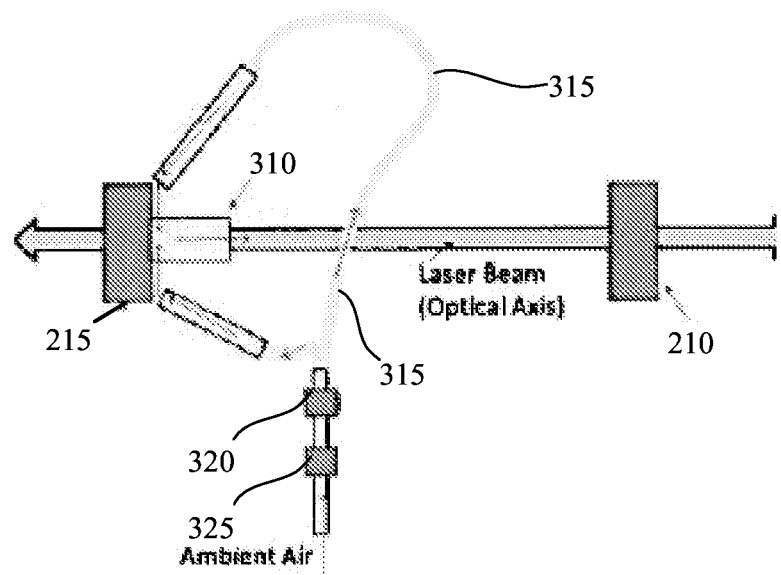

In some embodiments, it may be important to keep the reflectors 210 and 215 (and/or reflectors 110 and 120) clean during operation. FIG. 3A and FIG. 3B illustrate some techniques for keeping reflector 215 and/or reflector 210 clean. In some embodiments, purge air-flow system and/or protective irises (or baffles) 305 may be used to minimize exposure of the mirror surfaces to unfiltered ambient air, which may contain particulates or other contaminating constituents that degrade the mirror reflectivity.

The iris 305, for example, may geometrically block the ambient air (and its particles and contaminating elements) from reaching the mirror surface. The iris 305 and/or the mounting structures and/or supports may not block the light beam within the target volume. In some embodiments, for example, the iris 305 may be sized to be slightly bigger than the beam. An iris may be coupled with either or both reflector 210 and/or reflector 215. In some embodiments, a plurality of irises 305 may be disposed in any number of positions within the target volume and/or proximate the reflectors 210 and/or 215.

In some embodiments, a gas flow tube 310 may act as an extended iris 305. The gas flow tube 310 may be sized to be slightly larger than the beam. For example, the gas flow tube 310 or iris 305 may not occupy a large fraction of the target volume length to ensure that the flow of the sample air through/across the target volume is not impeded. In some embodiments, the diameter (or spot-size) of the light beam on reflectors 210 and/or 215 may be varied (e.g., reduced) to reduce the area on the reflector that is protected.

In some embodiments, a purge air-flow system may be used. A purge flow(s), for example, may form a protective layer(s) or film(s) on the mirror surfaces to minimize the contact of the ambient sample air on the mirror surfaces. Alternatively or additionally, the purge flow(s) may provide a small positive pressure region that reduces entry (diffusion) of ambient air to the region near the mirror surface. In some embodiments, contaminant-free air (or gases) may be used for purging and/or for films.

A purge air-flow system, for example, may include one or more air flow tubes 315, filter(s) 320 and/or pump(s) 325. Ambient air may be pumped into the air flow system using pump 325. The ambient air may flow through the filter 320 to remove particulates (and/or possibly other contaminating elements). The filtered ambient air may then be directed toward the inner surface of the reflector 210 and/or reflector 215. In some embodiments, the filter may include a particulate-filter, for example a HEPA (High-efficiency particulate air) filter, and or another filter with appropriate cut-off size. As another example, the filter may include a virtual impactor.

In some embodiments, the pump 325 may include a piezo-pump, a diaphragm pump, a fan, an axial fan, etc. to flow the ambient air over and/or through the filter(s) 320 and to direct the filtered ambient air to the mirror surfaces via the air flow tubes 315. As shown in FIG. 3B, pump 325 (or fan) may flow the ambient air through the filter 320 after which it may be split into multiple legs of the air flow tubes 315 and/or directed inside the gas flow tube 310 and/or then directed onto the mirror surface at approximately normal incidence. Such a configuration, for example, may be advantageous to ensure that the purge flow reaches the center region of the mirror where the laser beam may also incident.

As shown in FIG. 3B, the air flow tubes 315 are incident on the mirror surface at oblique angles (e.g., more parallel to the mirror surface). Alternatively or additionally, a positive pressure may also be created in an enclosure. For example, by sealing the gas flow tube 310 against the mirror, the inside of the gas flow tube 310 can have positive pressure to minimize entry of sample air inside (and therefore to the mirror surface). In some embodiments, compressed air or other gas rather than ambient air may be use. In some embodiments, the filter 320 and/or the pump 325 may be optionally removed.

Figure 4:
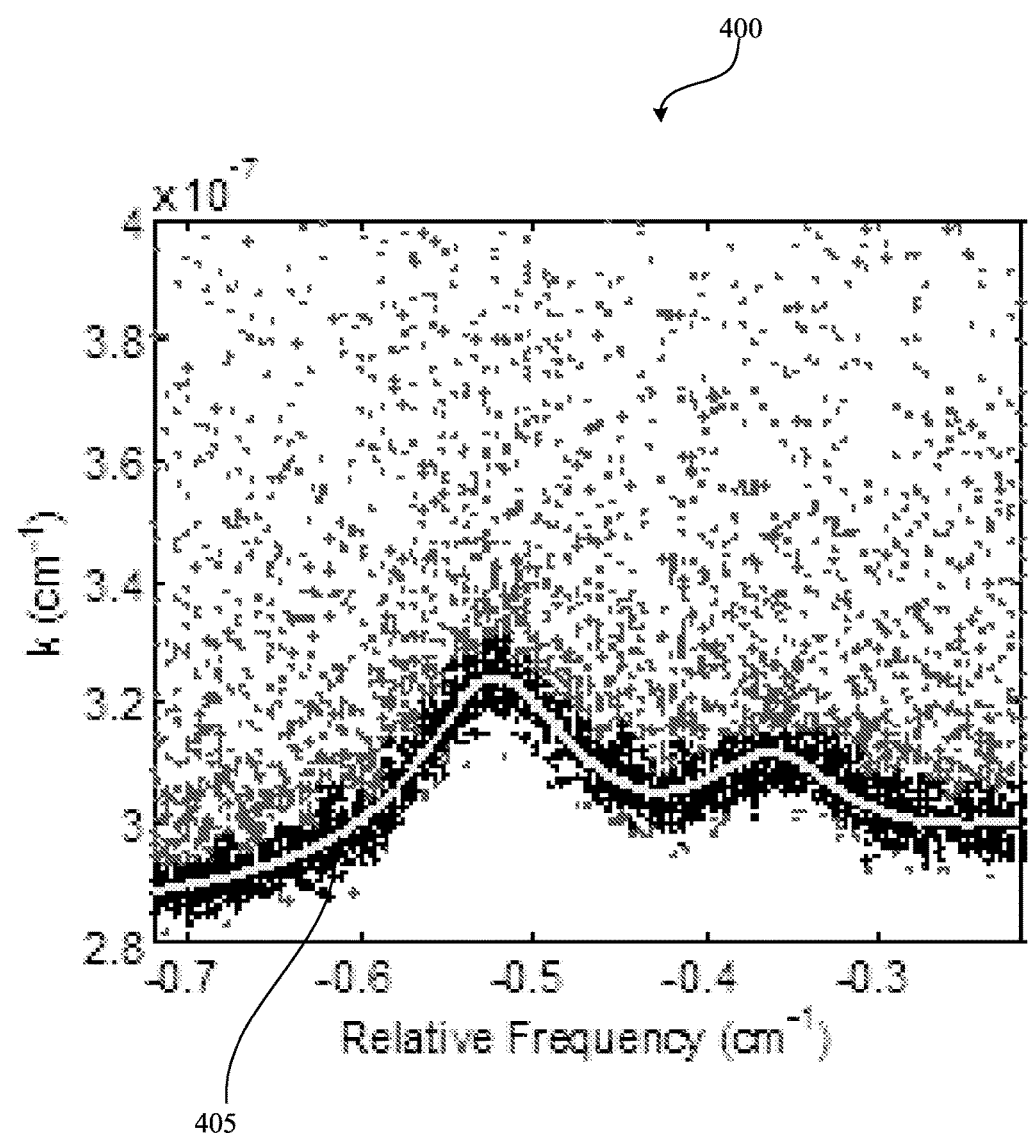
FIG. 4 is an example absorption spectrum of ambient laboratory air measured by a spectroscopy system according to some embodiments.

FIG. 4 is an example of a graph 400 of the absorption spectrum of ambient laboratory air measured by an open-path CRDS system according to some embodiments. The graph 400 shows the measured temporal decay (vertical-axis) vs. the relative frequency of the light source (horizontal-axis). The sampled points include noise introduced, for example, from the open nature of the spectroscopy system. The noise is shown throughout the graph 400. The fluctuations shown in the graph may be exclusively at the side of increased absorption, and may be attributed to the varying presence of larger particles (e.g., greater than about ~1-10 μm) within the laser beam volume of the target volume. Smaller particles (e.g., less than about 1 μm) which typically have weaker absorption and may be present at larger number densities with less statistical fluctuations, may manifest as a shift in the overall baseline, similar to a change in mirror reflectivity or a spectrally flat absorption. Embodiments described in this document, may be used to filter the noisy data and/or may aid in recovering the spectrum, which is shown by points near the spectral curve 405. A spectral curve 405 that is fit with the filtered points is shown in the graph.

Figure 5:
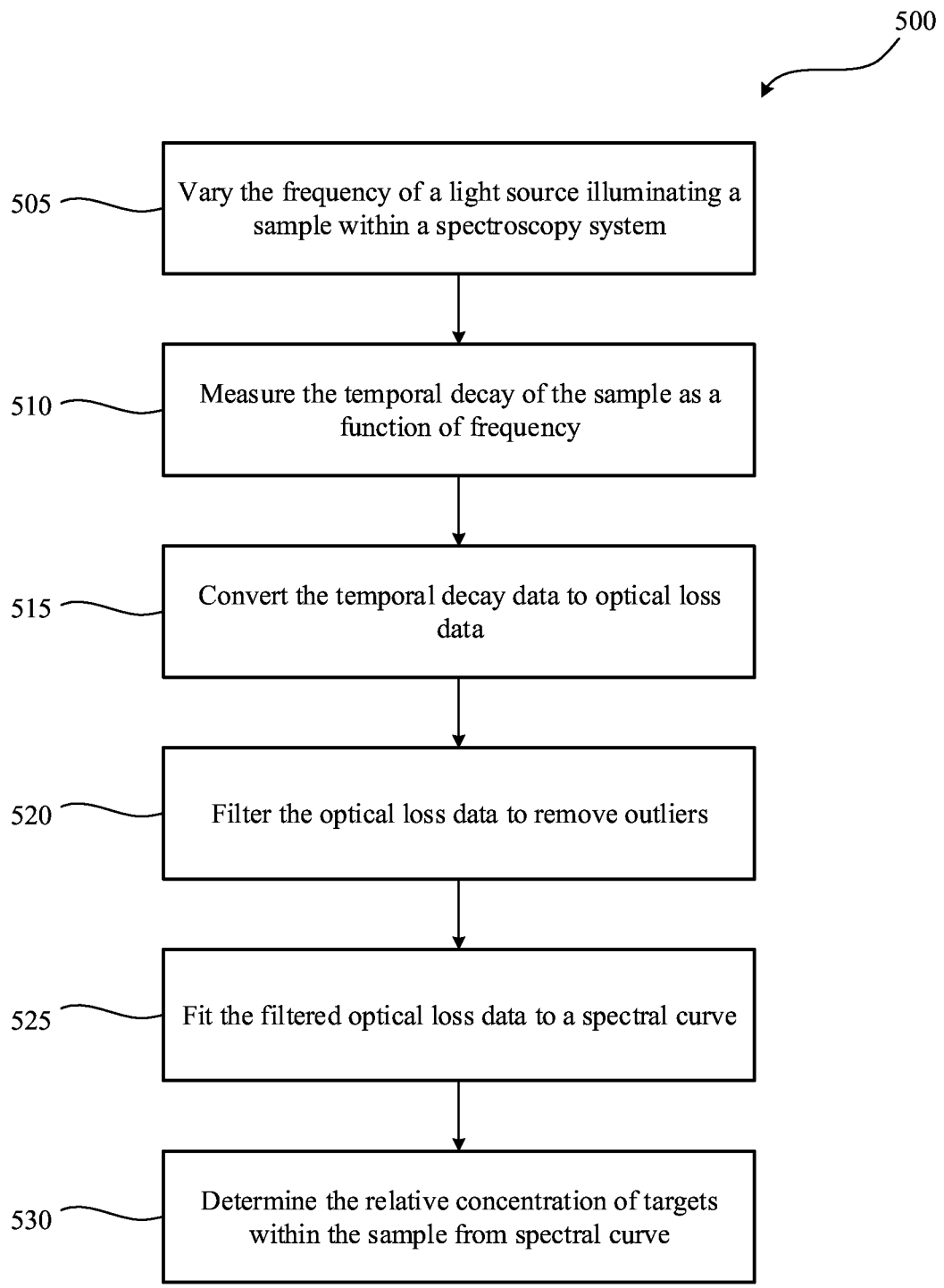
FIG. 5 is a flowchart of an example process for determining the concentration of targets within a sample using a spectroscopy system according to some embodiments.

FIG. 5 is a flowchart of an example process 500 for determining the concentration of targets within a sample according to some embodiments. One or more blocks of the process 500 may be implemented, in some embodiments, by one or more components of computational unit 1100 of FIG. 11. Although illustrated as discrete blocks, various blocks may be divided into additional blocks, combined into fewer blocks, or eliminated, depending on the desired implementation.

In some embodiments, process 500 may occur using computational unit 1100 in real time as data is sampled from a photo detector. Alternatively or additionally the process 500 may operate on data previously sampled using a photodetector that is stored in a digital storage location.

Process 500 begins at block 505. At block 505 the frequency of a light source illuminating a sample within a spectroscopy system may be varied. The light source, for example, may be light source 105 and/or light source 245. Alternatively or additionally the light source may be any light source used in a spectroscopy system such as, for example, the CRDS system 100 or CRDS system 200. The frequency of the light source, for example, may be varied across a known spectrum that may include one or more spectral lines indicative of the target species. The light source may be selected to produce light within the wavelength range that includes these spectral lines and/or may be scanned across one or more of the spectral lines indicative of the target. For example, the light source may be scanned with a linear or sinusoidal frequency variation at a rate of 10, 25, 50, 100, 250, 500, or 1,000 times per second. In some embodiments, the light from the light source may be extinguished with a modulator to measure the optical ring down time of the sample. In other embodiments, the light source may be turned off for periods of time to measure the optical ring down time of the sample.

At block 510 the temporal decay (or ring-down signal) of the sample may be measured (or determined). The temporal decay, for example, may be measured (or determined) from data sampled from a detector 125 or 205 after the beam has been extinguished or after the laser has rapidly scanned across a target volume resonance. In some embodiments, the temporal decay data may be sampled from the detector at a given sampling rate. In some embodiments, the temporal decay data may be sampled for each of the various frequencies of the light source. These temporal decay profiles may be converted to ring-down times. In some embodiments, the temporal decay data may be converted to optical loss data (or ring-down data) at block 515. The optical loss data, per pass through the target volume, can be found as the optical extinction loss, per pass through the target volume, as $1/(c*\tau)$. At block 520, the optical loss data may be filtered to remove outliers. The optical loss data may be filtered using any number or combination of techniques. For example, the optical loss data may be filtered using process 600, process 700, or process 1000 described in conjunction with FIG. 6, FIG. 7 and FIG. 10 respectively.

At block 525 the filtered optical loss data may be fit with a spectral curve using any number of curve fitting techniques. For example, a spectral curve may be fit with the filtered optical loss data using any type of regression algorithm, least squares fit algorithm, Levenberg-Marquardt algorithm etc. Alternatively or additionally the filtered optical loss data may be fit with a Gaussian function, a Lorentzian function, a Voigt function, or sum of the aforementioned functions via regression methods (for example, Least Squares etc. as listed above). In some embodiments, the optical loss data used to fit the optical loss data to a spectral curve may be filtered based on process 600, process 700, or process 1000. Fitting of the spectral curve may also require knowledge of temperature and/or pressure within the target volume. The temperature and/or pressure may be measured, for example, by transducers in the target volume. Alternatively or additionally the temperature and/or pressure may be assumed to be fixed or determined by other means.

At block 530 the concentration of targets within the sample may be determined from the spectral curve.

Figure 6:
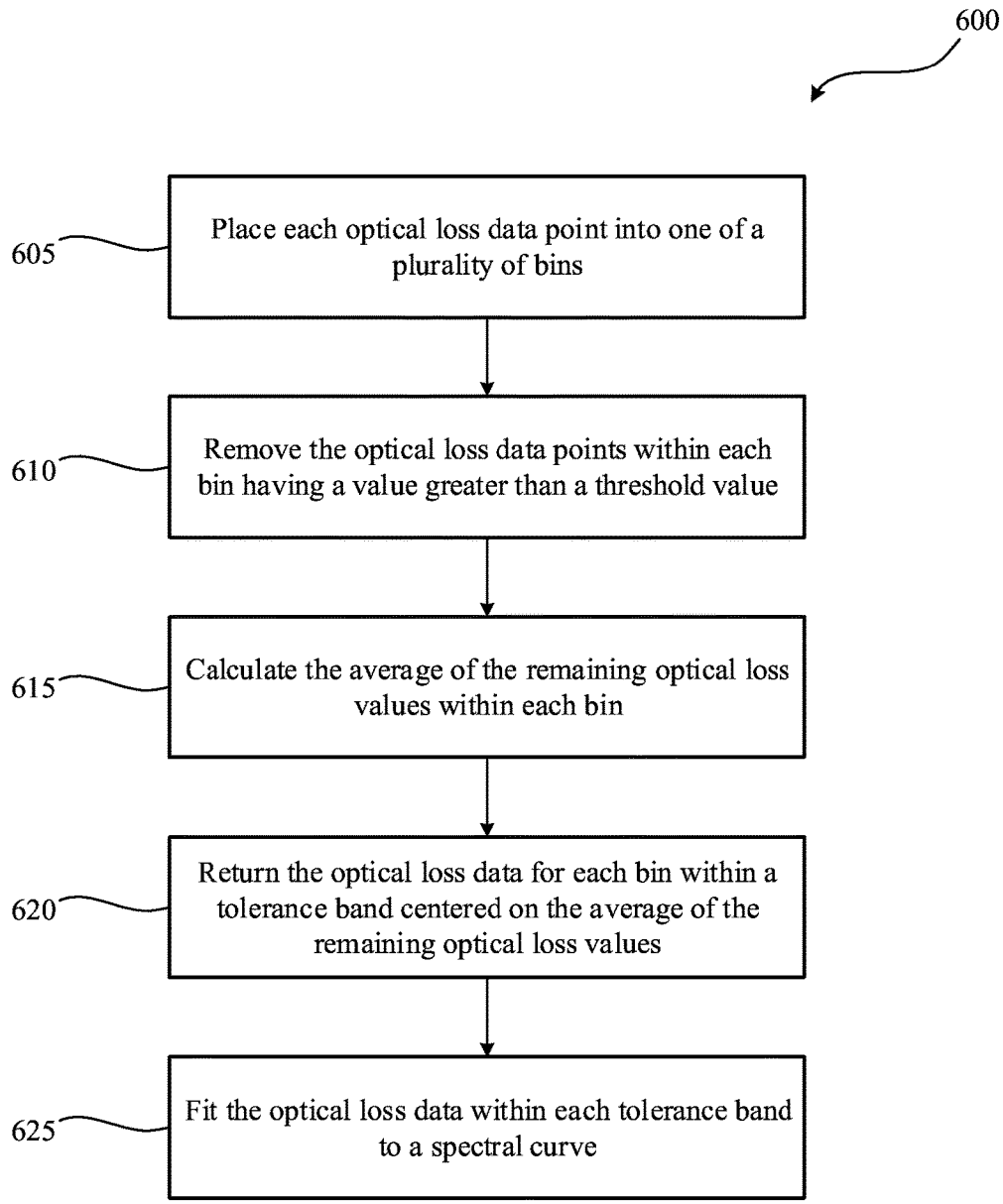
FIG. 6 is a flowchart of an example process for filtering optical loss data to remove optical loss data outliers using a spectroscopy system according to some embodiments.

FIG. 6 is a flowchart of an example process 600 for filtering optical loss data to remove outliers according to some embodiments. One or more blocks of the process 600 may be implemented, in some embodiments, by one or more components of computational unit 1100 of FIG. 11. Although illustrated as discrete blocks, various blocks may be divided into additional blocks, combined into fewer blocks, or eliminated, depending on the desired implementation.

In some embodiments, process 600 may occur using computational unit 1100 in real time as data is sampled from a photo detector. Alternatively or additionally the process 600 may operate on data previously sampled using a photodetector that is stored in a digital storage location.

Process 600 begins at block 605 where each optical loss data point is placed into one of a plurality of bins. Each bin, for example, may include optical loss data recorded within a given frequency interval that is part of the laser scan range. Each frequency bin may have a fixed width. For example, each frequency band may have a predetermined fixed width, for example, of 0.1 GHz.

At block 610 in each bin, the optical loss data points having a value greater than a threshold value may be discarded. In some embodiments, the threshold value may be predetermined value for each bin or for all the bins. In some embodiments, the threshold value may be a unique value that is determined for each bin. In some embodiments, a predetermined percentage of data points such as, for example, 30%, 40%, 50%, 60%, 70%, etc. with the lowest values of optical loss are maintained, while the remaining values (with higher loss) are discarded. The predetermined value may be a value that is a percentage of the spread in the bin plus the average, or a percentage of the average of the bin, etc. Regardless, block 610 may return a subset of the optical loss values in each bin.

At block 615, an average of the subset of the optical loss values (or remaining optical loss values) in each bin may be calculated. The average, for example, may include any type of statistical centering such as, for example, the mean, the median, etc. of the subset of the optical loss values in each bin. In some embodiments, the standard deviation, variation, dispersion, etc. from the average may also be returned.

At block 620 the optical loss data for each bin within a tolerance band centered on the average of the subset optical loss values is reserved, with the remaining points rejected. The tolerance band, for example, may include values within a predetermined number of standard deviations (e.g., two or three standard deviations). Alternatively or additionally the tolerance band may be a function of a statistical measure such as, for example, the deviation, variation, dispersion, etc. centered on the average of the subset of the optical loss values in each bin.

At block 625 the optical loss data within each tolerance band may be used to fit the optical loss data to a spectral curve using any number of curve fitting techniques. For example, a spectral curve may be fit with the filtered optical loss data using any type of regression algorithm, least squares fit algorithm, Levenberg-Marquardt algorithm etc. Alternatively or additionally the filtered optical loss data may be fit with a Gaussian function, a Lorentzian function, a Voigt function, or a sum of the aforementioned functions via regression methods.

Figure 7:
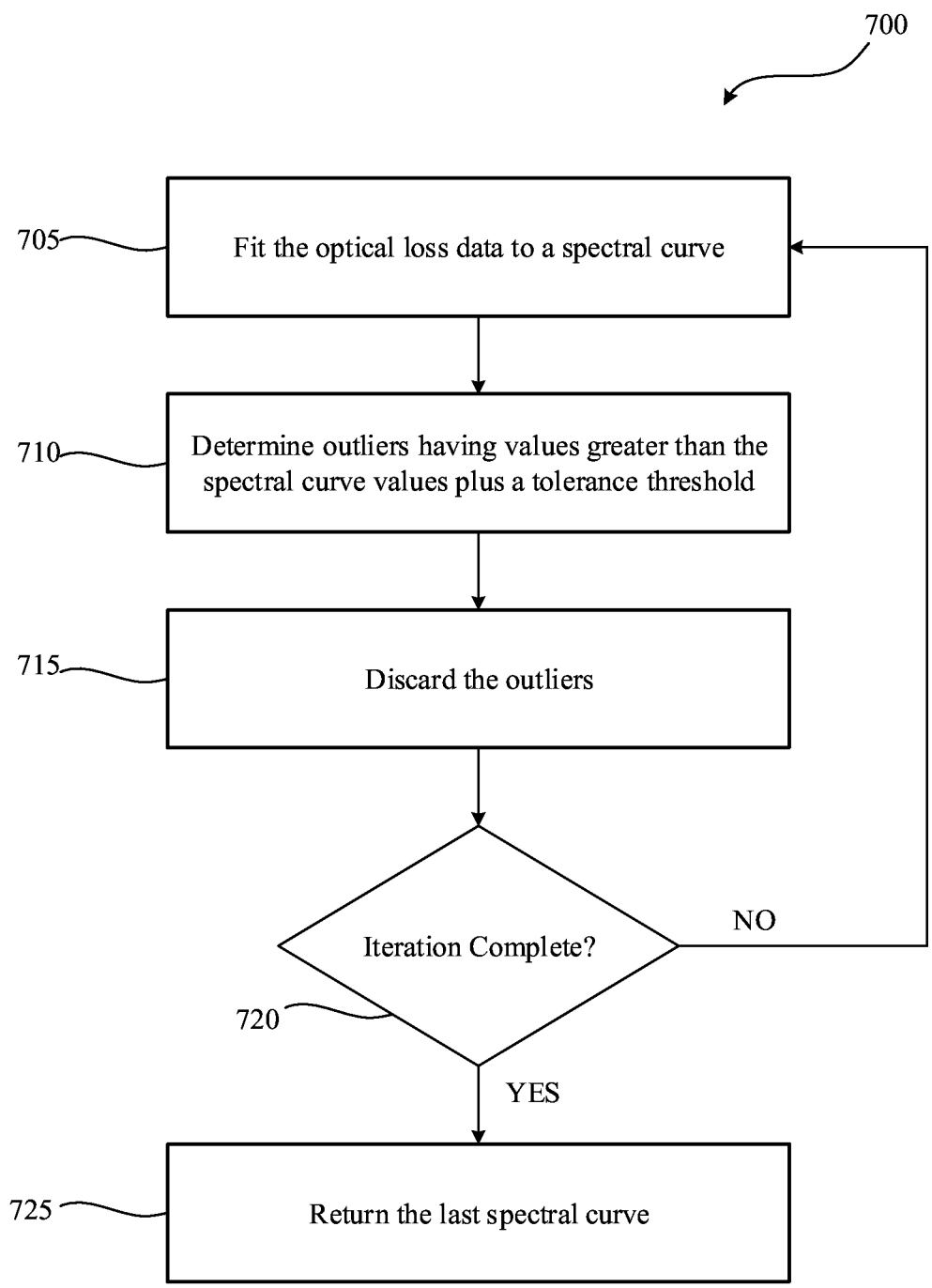
FIG. 7 is a flowchart of an example process for filtering optical loss data using an iterative technique to remove optical loss data outliers using a spectroscopy system according to some embodiments.

FIG. 7 is a flowchart of another example process 700 for filtering optical loss data using an iterative technique to remove outliers according to some embodiments. One or more blocks of the process 700 may be implemented, in some embodiments, by one or more components of computational unit 1100 of FIG. 11. Although illustrated as discrete blocks, various blocks may be divided into additional blocks, combined into fewer blocks, or eliminated, depending on the desired implementation.

In some embodiments, process 700 may occur using computational unit 1100 in real time as data is sampled from a photo detector. Alternatively or additionally the process 700 may operate on data previously sampled using a photodetector that is stored in a digital storage location.

Process 700 may begin at block 705. At block 705 a spectral curve may be fit with the optical loss data using any number of curve fitting techniques. For example, a spectral curve may be fit with the filtered optical loss data using any type of regression algorithm, least squares fit algorithm, Levenberg-Marquardt algorithm etc. Alternatively or additionally the filtered optical loss data may be fit with a Gaussian function, a Lorentzian function, a Voigt function, or a sum of the aforementioned functions via regression methods.

At block 710 data points for each frequency having a value greater than the spectral curve value for the given frequency plus a positive tolerance threshold value may be considered outliers. The tolerance threshold value, for example, may include a value that is a linear function of a standard deviation, variation, dispersion, etc. of the spectral curve or the optical loss data for all or the given frequency. Alternatively or additionally, the tolerance threshold value may include a fixed value.

At block 715, the outliers may be discarded.

At block 720 it may be determined whether the iterative technique is complete. For example, if only a single spectral curve has been fit with the data, then the iteration is not complete and process 700 returns to block 705 wherein the optical loss data with the outliers removed is used to fit a spectral curve. Otherwise process 700 proceeds to block 725.

Alternatively or additionally, at block 720, if the number of iterations exceeds or equals a maximum number of iterations then process 700 proceeds to block 725. Otherwise, process 700 returns to block 705 wherein the optical loss data with the outliers removed is used to fit a spectral curve.

Figure 9:
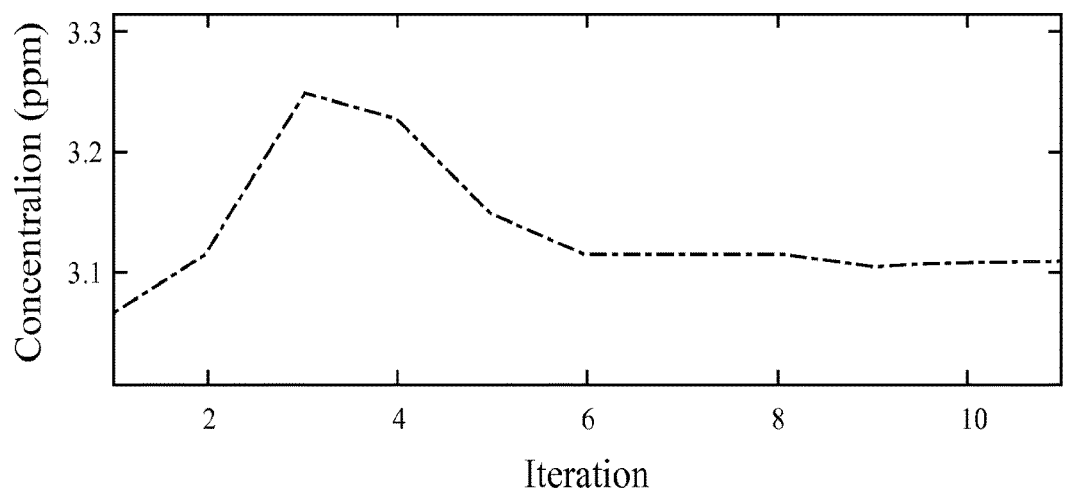
FIG. 9 is a graph of the concentration calculated for each iteration in process shown in FIG. 7.

Alternatively or additionally, at block 720, the spectral curve may be used to determine the concentration of a target within the sample. If the difference in concentration calculated using the current spectral curve and the concentration calculated using the previous spectral curve is less than a concentration threshold value, then process 700 proceeds to block 725. Otherwise, process 700 returns to block 705 wherein the optical loss data with the outliers removed is used to fit a spectral curve. The concentration threshold value, for example, may include 0.5, 0.1, 0.05, 0.01, 0.005, 0.001 PPM, etc. A graph showing convergence based on the calculated concentration difference is shown in FIG. 9.

Alternatively or additionally, at block 720, the quality of the fit created in block 705 may be determined. The quality of the fit may be determined, for example, using any statistical hypothesis test. In some embodiments, a chi squared test may be used. If the chi squared value of the fit is below a threshold value, then the iteration is complete and process 700 proceeds to block 725. Otherwise, process 700 returns to block 705 wherein the optical loss data with the outliers removed is used to fit a spectral curve.

Figure 8:
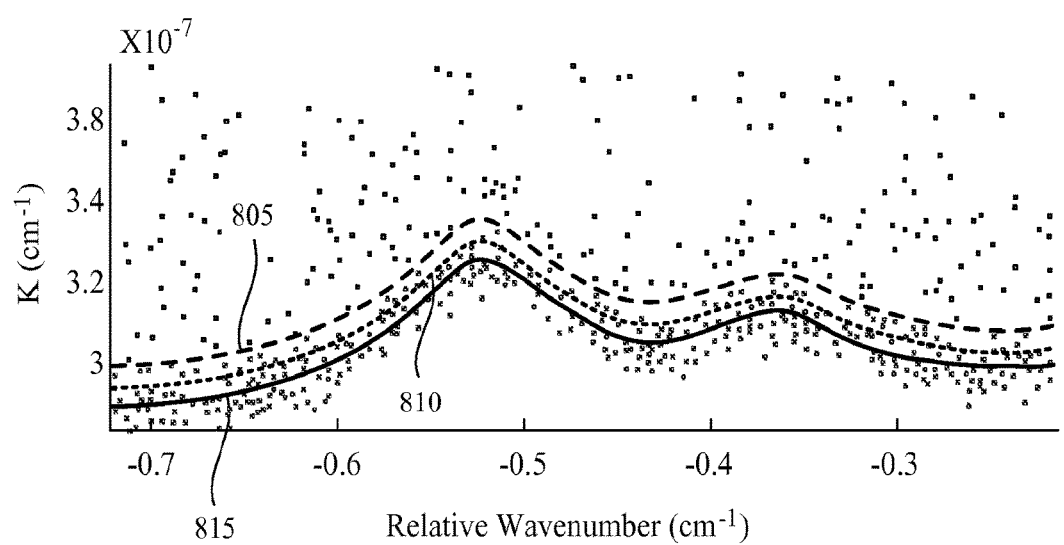
FIG. 8 is a graph of portions of the iterative technique.

Various other techniques may be used singularly or in combination to determine whether the iterative process is complete, at block 720. These techniques, for example, may include techniques to determine whether a convergence in the concentration values has been found. At block 725 the last spectral curve found at block 705 may be returned and/or the concentration of a target within the sample may be determined using the last spectral curve. FIG. 8 is a graph of portions of the iterative technique shown in FIG. 7. At block 705, for example, a spectral curve 810 (the dashed line) may be determined. The spectral curve plus the tolerance threshold 805 is shown as a dotted line. All the data points above the spectral curve plus the tolerance threshold 805 are discarded. This process is repeated until the iteration is complete and the spectral curve 815 is returned.

In some embodiments, after an iteration criterion is reached, at block 710 can determine outliers having values greater than the spectral curve values plus a tolerance threshold and determine outliers having values less than the spectral curve values minus a second tolerance threshold. In some embodiments, the second tolerance threshold may be the same value as the tolerance threshold or have a different value. In some embodiments, the iteration criterion, for example, may be a number of iterations greater than one.

FIG. 9 is a graph of the concentration calculated for a plurality of iterations in the process 700. As shown in the graph, the concentration tends towards convergence as the number of iterations increases.

Figure 10:
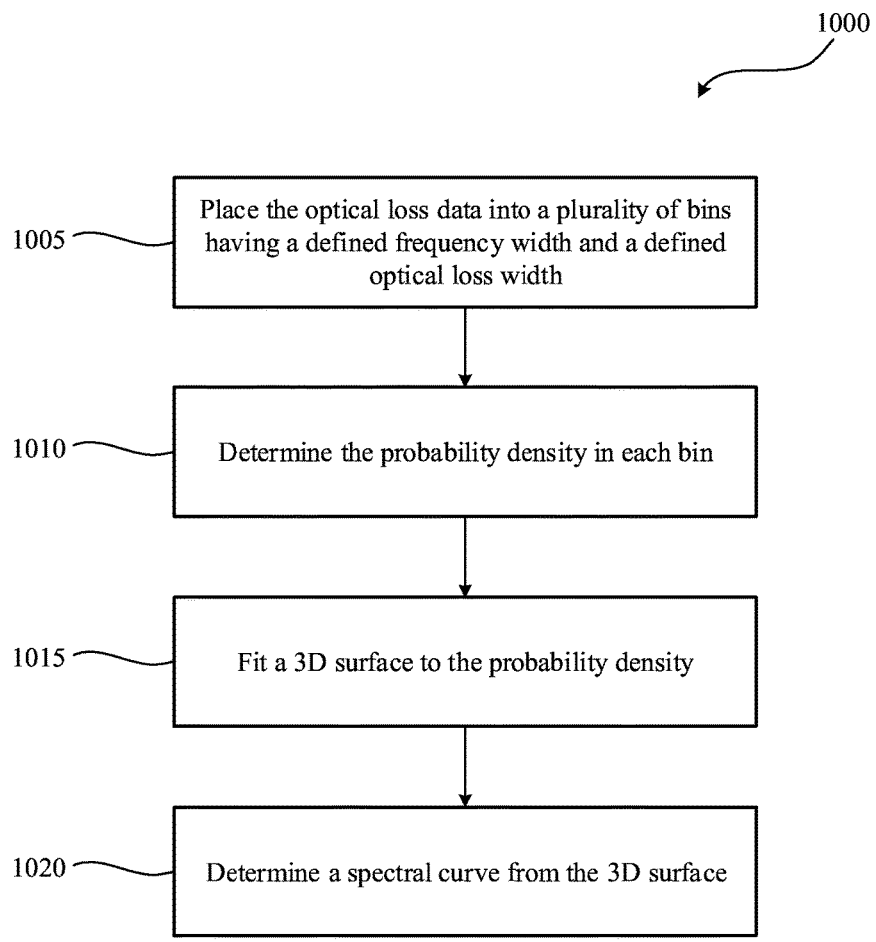
FIG. 10 is a flowchart of an example process for filtering optical loss data to produce a spectral curve using a three-dimensional surface curve according to some embodiments.

FIG. 10 is a flowchart of an example process 1000 for filtering optical loss data to produce a spectral curve using a three-dimensional surface curve according to some embodiments. One or more blocks of the process 1000 may be implemented, in some embodiments, by one or more components of computational unit 1100 of FIG. 11. Although illustrated as discrete blocks, various blocks may be divided into additional blocks, combined into fewer blocks, or eliminated, depending on the desired implementation.

In some embodiments, process 1000 may occur using computational unit 1100 in real time as data is sampled from a photo detector. Alternatively or additionally the process 1000 may operate on data previously sampled using a photodetector that is stored in a digital storage location.

Process 1000 begins at block 1005. At block 1005 each optical loss data point may be placed into one of a plurality of bins. Each bin may have a defined frequency width and a defined optical loss width. Each bin, for example, may include optical loss data recorded within a given frequency band and a given optical loss band. For example, each frequency band may include optical loss data points recorded with a frequency within the respective frequency band and each optical loss band may include optical loss data points recorded having an optical loss value within the respective optical loss band. Each frequency band may have a fixed width. For example, each frequency band may have a predetermined fixed width. Each optical loss band may have a fixed width. For example, each optical loss band may have a predetermined fixed width.

At block 1010 a count value may be determined for each bin. The count value, for example, may be determined from the number of data points found within each bin. The probability density may include a mapping of all the count values. The probability density, for example, may result, for example, in a three-dimensional map of optical loss values within each bin.

At block 1015 a three-dimensional surface may be fit with the probability density using, for example, a surface fit function. The surface, which represents the probability density, may be a function of both the frequency and the optical loss. Various mathematical forms can be used including Gaussian dependences along the loss coordinate and spectral functions, including sums of Lorentzian and/or Gaussians and/or Voigts, along the frequency coordinate. The spectral function along the frequency coordinate may contain the concentrations of the target species. In some embodiments, the fit function may use the concentration as one of the fit parameters.

At block 1020 the three-dimensional surface may be used to fit the optical loss data to a spectral curve using any number of curve fitting techniques. For example, a spectral curve may be fit with the filtered optical loss data using any type of regression algorithm, least squares fit algorithm, Levenberg-Marquardt algorithm etc. Alternatively or additionally the filtered optical loss data may be fit with a Gaussian function, a Lorentzian function, a Voigt function, or a sum of the aforementioned functions via regression methods (for example, Least Squares etc. as listed above).

In some embodiments, the spectral curve determined from the probability density, for example, according to process 1000, may consider both the spectral shape (in frequency and absorption space) as well as the Gaussian spread of the measurements (in absorption and/or probability density space).

Figure 11:
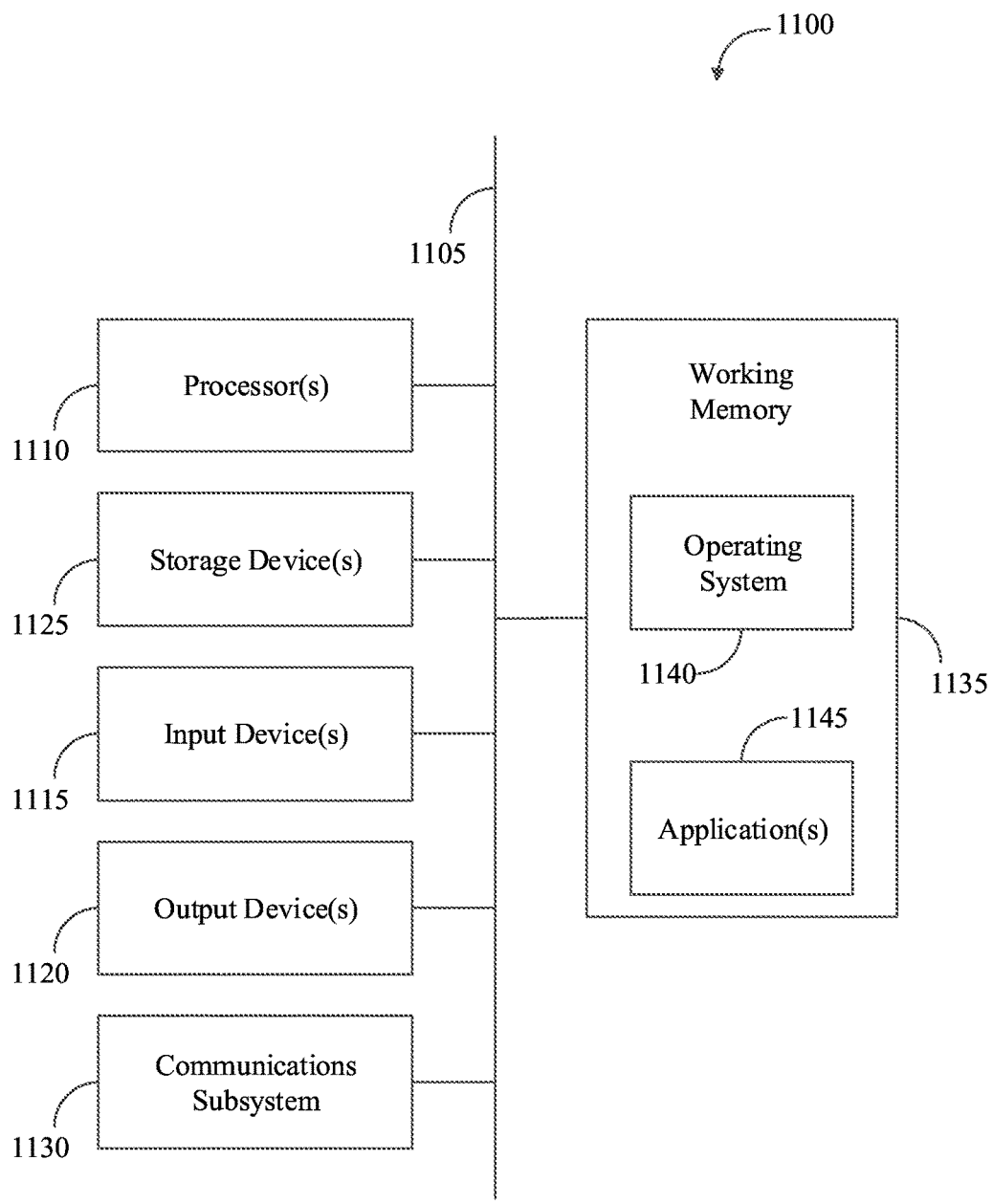
FIG. 11 shows an illustrative computational system for performing functionality to facilitate implementation of embodiments described herein.

The computational unit 1100 (or processing unit) illustrated in FIG. 11 can be used to perform and/or control operation of any of the embodiments described herein. For example, the computational unit 1100 can be used alone or in conjunction with other components. As another example, the computational unit 1100 can be used to perform any calculation, solve any equation, perform any identification, and/or make any determination described here.

The computational unit 1100 may include any or all of the hardware elements shown in the figure and described herein. The computational unit 1100 may include hardware elements that can be electrically coupled via a bus 1105 (or may otherwise be in communication, as appropriate). The hardware elements can include one or more processors 1110, including, without limitation, one or more general-purpose processors and/or one or more special-purpose processors (such as digital signal processing chips, graphics acceleration chips, and/or the like); one or more input devices 1115, which can include, without limitation, a mouse, a keyboard, and/or the like; and one or more output devices 1120, which can include, without limitation, a display device, a printer, and/or the like.

The computational unit 1100 may further include (and/or be in communication with) one or more storage devices 1125, which can include, without limitation, local and/or network-accessible storage and/or can include, without limitation, a disk drive, a drive array, an optical storage device, a solid-state storage device, such as random access memory ("RAM") and/or read-only memory ("ROM"), which can be programmable, flash-updateable, and/or the like. The computational unit 1100 might also include a communications subsystem 1130, which can include, without limitation, a modem, a network card (wireless or wired), an infrared communication device, a wireless communication device, and/or chipset (such as a Bluetooth® device, a 802.6 device, a Wi-Fi device, a WiMAX device, cellular communication facilities, etc.), and/or the like. The communications subsystem 1130 may permit data to be exchanged with a network (such as the network described below, to name one example) and/or any other devices described herein. In many embodiments, the computational unit 1100 will further include a working memory 1135, which can include a RAM or ROM device, as described above.

The computational unit 1100 also can include software elements, shown as being currently located within the working memory 1135, including an operating system 1140 and/or other code, such as one or more application programs 1145, which may include computer programs of the invention, and/or may be designed to implement methods of the invention and/or configure systems of the invention, as described herein. For example, one or more procedures described with respect to the method(s) discussed above might be implemented as code and/or instructions executable by a computer (and/or a processor within a computer). A set of these instructions and/or codes might be stored on a computer-readable storage medium, such as the storage device(s) 1125 described above.

In some cases, the storage medium might be incorporated within the computational unit 1100 or in communication with the computational system 1100. In other embodiments, the storage medium might be separate from the computational unit 1100 (e.g., a removable medium, such as a compact disc, etc.), and/or provided in an installation package, such that the storage medium can be used to program a general-purpose computer with the instructions/code stored thereon. These instructions might take the form of executable code, which is executable by the computational unit 1100 and/or might take the form of source and/or installable code, which, upon compilation and/or installation on the computational unit 1100 (e.g., using any of a variety of generally available compilers, installation programs, compression/decompression utilities, etc.), then takes the form of executable code.

The term "substantially" means within 5% or 10% of the value referred to or within manufacturing tolerances.

Various embodiments are disclosed. The various embodiments may be partially or completely combined to produce other embodiments.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Some portions are presented in terms of algorithms or symbolic representations of operations on data bits or binary digital signals stored within a computing system memory, such as a computer memory. These algorithmic descriptions or representations are examples of techniques used by those of ordinary skill in the data processing art to convey the substance of their work to others skilled in the art. An algorithm is a self-consistent sequence of operations or similar processing leading to a desired result. In this context, operations or processing involves physical manipulation of physical quantities. Typically, although not necessarily, such quantities may take the form of electrical or magnetic signals capable of being stored, transferred, combined, compared, or otherwise manipulated. It has proven convenient at times, principally for reasons of common usage, to refer to such signals as bits, data, values, elements, symbols, characters, terms, numbers, numerals, or the like. It should be understood, however, that all of these and similar terms are to be associated with appropriate physical quantities and are merely convenient labels. Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical, electronic, or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general-purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

Embodiments of the methods disclosed herein may be performed in the operation of such computing devices. The order of the blocks presented in the examples above can be varied—for example, blocks can be re-ordered, combined, and/or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

While the present subject matter has been described in detail with respect to specific embodiments thereof, it will be appreciated that those skilled in the art, upon attaining an understanding of the foregoing, may readily produce alterations to, variations of, and equivalents to such embodiments. Accordingly, it should be understood that the present disclosure has been presented for-purposes of example rather than limitation, and does not preclude inclusion of such modifications, variations, and/or additions to the present subject matter as would be readily apparent to one of ordinary skill in the art.

That which is claimed:

1. A method to determine a concentration of a species within a sample using an open path cavity ring-down spectroscopy system, the method comprising:
   emitting, by a light source, a light beam;
   directing the light beam emitted by the light source through a sample positioned between two reflectors;
   collecting, using an open path cavity ring-down spectroscopy system, temporal decay data of the light beam as the light beam reflects back and forth through the sample between the two reflectors;

converting, using the open path cavity ring-down spectroscopy system, the temporal decay data to optical loss data, the optical loss data including optical loss data over a range of frequencies;

placing the optical loss data into a plurality of bins, each bin having a defined frequency width;

determining an average optical loss data value for each bin from a subset of optical loss data values within each bin;

removing the optical loss data within each bin having a value outside a tolerance range bounding the average optical loss data value for the respective bin;

after the removing, fitting a spectral curve to the remaining optical loss data; and determining the concentration of the species within the sample based on the spectral curve, wherein the subset of optical loss data values within each bin comprises optical loss data values within the respective bin below a threshold value.

2. The method according to claim 1, wherein the concentration of the species within the sample is determined based on spectral peaks within the spectral curve.

3. The method according to claim 1, wherein fitting the spectral curve to the remaining optical loss data comprises fitting the spectral curve to the remaining optical loss data using a least squares technique.

4. A method to determine a concentration of a species within a sample using an open path cavity ring-down spectroscopy system, the method comprising:

emitting, by a light source, a light beam;

directing the light beam emitted by the light source through a sample positioned between two reflectors;

collecting, using an open path cavity ring-down spectroscopy system, temporal decay data of the light beam as the light beam reflects back and forth through the sample between the two reflectors;

converting, using the open path cavity ring-down spectroscopy system, the temporal decay data to optical loss data, the optical loss data including optical loss data over a range of frequencies;

placing the optical loss data into a plurality of bins, each bin having a defined frequency width;

determining an average optical loss data value for each bin from a subset of optical loss data values within each bin;

removing the optical loss data within each bin having a value outside a tolerance range bounding the average optical loss data value for the respective bin;

after the removing, fitting a spectral curve to the remaining optical loss data; and determining the concentration of the species within the sample based on the spectral curve, wherein the subset of optical loss data values within each bin comprises a predetermined percentage of the optical loss data values having the lowest optical loss data value.

5. The method according to claim 4, wherein the concentration of the species within the sample is determined based on spectral peaks within the spectral curve.

6. The method according to claim 4, wherein fitting the spectral curve to the remaining optical loss data comprises fitting the spectral curve to the remaining optical loss data using a least squares technique.

* * * * *